(12) United States Patent
Ko et al.

(10) Patent No.: US 9,757,409 B2
(45) Date of Patent: Sep. 12, 2017

(54) METHOD TO PREPARE GANODERMA LUCIDUM POLYSACCHARIDES POSSESSING INSULIN-SENSITIZING PROPERTIES AND APPLICATIONS THEREOF

(71) Applicant: Chang Gung Biotechnology Corp., Taipei (TW)

(72) Inventors: Yun-Fei Ko, Taipei (TW); Jan Martel, Taipei (TW); Jian-Ching Liau, Taipei (TW); I-Te Chang, Taipei (TW); Wei-Ting Jian, Taipei (TW); Mei-Feng Lin, Taipei (TW); Chia-Jen Yang, Taipei (TW); Chen-Yaw Chiu, Taipei (TW); Chih-Jung Chang, Taipei (TW); Chuan-Sheng Lin, Taipei (TW); Tsung-Ru Wu, Taipei (TW); Chia-Chen Lu, Taipei (TW); David Marcelo Ojcius, Taipei (TW); Hsin-Chih Lai, Taipei (TW); John D. Young, Taipei (TW)

(73) Assignee: Chang Gung Biotechnology Corp., Taipei (TW)

( * ) Notice: Subject to any disclaimer, the term of this patent is extended or adjusted under 35 U.S.C. 154(b) by 13 days.

(21) Appl. No.: 14/855,055

(22) Filed: Sep. 15, 2015

(65) Prior Publication Data
US 2016/0354405 A1   Dec. 8, 2016

(30) Foreign Application Priority Data
Jun. 5, 2015 (TW) .............................. 104118337 A

(51) Int. Cl.
*A61K 31/715* (2006.01)
*A61K 36/074* (2006.01)
*C08B 37/00* (2006.01)

(52) U.S. Cl.
CPC .......... *A61K 31/715* (2013.01); *A61K 36/074* (2013.01); *C08B 37/0003* (2013.01); *A61K 2236/00* (2013.01)

(58) Field of Classification Search
CPC ........................... A61K 31/715; A61K 36/074
See application file for complete search history.

(56) References Cited

PUBLICATIONS

Zhang et al., Acta Pharmacol. Sin., 2004, 25(2), p. 191-195.*
Xiao et al., Arch. Pharm. Res., 2012, 35(10), p. 1793-1801.*
Sun et al., Carbohydr. Polym., 2014, 114, p. 432-439.*
Zhao et al. Carbohydr. Polym., 2010, 80, p. 783-789.*
Chih-Jung Chang et al, Ganoderma lucidum reduces obesity in mice by modulating the composition of the gut microbiota, Nature Communications | 6:7489 | DOI: 10.1038/ncomms8489.

* cited by examiner

*Primary Examiner* — Jonathan S Lau
(74) *Attorney, Agent, or Firm* — WPAT, P.C., Intellectual Property Attorneys; Anthony King

(57) ABSTRACT

The present invention provides a method to prepare polysaccharides from *Ganoderma lucidum*. The prepared polysaccharides can reduce hyperglycemia and improve insulin sensitivity in humans and animals, and can therefore be used to prevent and treat type 2 diabetes.

8 Claims, 10 Drawing Sheets

METHOD TO PREPARE GANODERMA LUCIDUM POLYSACCHARIDES POSSESSING INSULIN-SENSITIZING PROPERTIES AND APPLICATIONS THEREOF

CROSS-REFERENCE TO RELATED APPLICATION

This application claims priority of Taiwan patent application No. 104118337, filed on Jun. 5, 2015, the content of which is incorporated herein in its entirety by reference.

BACKGROUND OF THE INVENTION

1. Field of the Invention

The present invention relates to compositions and methods for improving insulin sensitivity. Particularly, the present invention provides methods for improving insulin sensitivity by using a polysaccharide isolated from *Ganoderma lucidum* as well as methods for preparing the polysaccharide.

2. The Prior Art

Type 2 diabetes mellitus is a disease characterized by a failure to regulate blood glucose levels. In the long term, this condition may lead to several complications, including cardiovascular disease, eye damage, foot ulcers, kidney failure, and stroke. The high prevalence of diabetes is currently a major threat to public health, with an estimated 387 million diabetic people worldwide. As a result, prevention of diabetes represents a major challenge for modern societies.

In early stage type 2 diabetes, peripheral tissues such as the liver, muscles, and fat tissues show reduced sensitivity to insulin. At this stage, a number of treatments can be used to stabilize blood glucose levels, including diet monitoring, regular exercise, and medications. Metformin is a synthetic drug that decreases hyperglycemia by suppressing glucose production by the liver. In addition, this drug increases sensitivity to insulin in peripheral tissues and decreases absorption of glucose by the intestinal tract. However, metformin and other anti-diabetic medications produce side-effects, including diarrhea and other gastric disorders, kidney dysfunction, liver disease, nausea, skin rash, and urinary tract infections, which may limit treatment compliance and efficacy.

In view of the growing incidence of diabetes in the human population and the difficulties observed regarding prevention and treatment, there is a need for alternative measures to prevent, treat and control this disease. New measures that can be introduced in the diet without necessitating major lifestyle changes and without incurring in toxicity or adverse effects are particularly needed.

SUMMARY OF THE INVENTION

The present invention provides a method for improving insulin sensitivity, comprising administrating an effective amount of a polysaccharide isolated from *Ganoderma lucidum* to a subject, wherein the polysaccharide has a molecular weight above 135 kDa and contains at least mannose, glucose, and galactose. The polysaccharide further contains fucose, rhamnose, arabinose, and glucosamine. In one embodiment of the present invention, a weight ratio of fucose, rhamnose, arabinose, glucosamine, galactose, glucose, and mannose in the polysaccharide ranges between 2:2:2:1:16:26:47 and 3:3:3:1:17:27:48. The polysaccharide of the present invention has a molecular weight ranging from 135 kDa to 5,364 kDa, an average molecular weight of 846 kDa, with a polydispersity index of 6.25. The polysaccharide reduces fasting serum insulin, fasting blood glucose, and insulin resistance levels of the subject. In one embodiment of the present invention, the effective amount of the polysaccharide described in the present invention is from 0.001 mg/kg to 1 g/kg per day. Preferably, the effective daily amount or dosage of *G. lucidum* polysaccharide given to a human subject (with an average weight of 70 kg) is 4.53 g (0.0646 g per kilogram of body weight).

In another aspect, the present invention provides a method to prepare the polysaccharide isolated from *G. lucidum*, comprising the following steps: extracting dried *G. lucidum* mycelium with water; inducing the formation of a precipitate by adding an alcohol; isolating the precipitate by centrifugation; and fractionating the precipitate by filtration. Specifically, the present invention provides a method comprising: (a) mixing the *G. lucidum* mycelium with water to give a first mixture, extracting the first mixture for a first predetermined time under a low-speed rotation to give a supernatant, and concentrating the supernatant to obtain a concentrated *G. lucidum* extract; (b) adding an alcohol to the concentrated *G. lucidum* extract to give a second mixture, allowing the second mixture to stand for a second predetermined time and produce a precipitate to obtain a crude *G. lucidum* polysaccharide extract; (c) isolating the crude *G. lucidum* polysaccharide extract with centrifugation, and fractionating the crude polysaccharide extract using tangential flow filtration (TFF) to obtain a *G. lucidum* polysaccharide.

In one embodiment of the present invention, for step (a), the supernatant is concentrated using a vacuum concentrator and the *G. lucidum* mycelium is mixed with water at a ratio of 5% (w/v). For step (b), the alcohol is 95% ethanol, the concentration of the concentrated *G. lucidum* extract is 20% (w/v), the concentrated *G. lucidum* extract is mixed with 95% ethanol at a ratio of 1:5, and the second predetermined time is at least 16 hours. For step (c), *G. lucidum* polysaccharides are fractionated using TFF with a 0.2-nm hollow fiber membrane and 10-to-300-kDa cassette membranes (50 cm$^2$, polyethersulfone, PES).

The *G. lucidum* polysaccharide described in the present invention can reduce hyperglycemia and improve insulin sensitivity in humans and animals; therefore, the polysaccharide can be utilized as a drug, a supplement, a food, or a drink for the treatment or prevention of type 2 diabetes mellitus or other diseases involving dysregulation of blood sugar homeostasis.

The present invention is further explained in the following drawings and examples. It is understood that the examples given below do not, however, limit the scope of the invention, and it will be evident to those skilled in the art that modifications can be made without departing from the scope of the appended claims.

DETAILED DESCRIPTION OF THE PREFERRED EMBODIMENT

Definition

The "effective amount" described in the present invention refers to the dosage of polysaccharide that can reduce fasting serum insulin, fasting blood glucose, insulin resistance, and glucose intolerance levels in animals and humans. The appropriate effective dosage may vary depending on the organism or individual treated but can be determined experimentally using various techniques, including a dose escalation study.

The data provided in the present invention represent approximated, experimental values that may vary within a range of ±20%, preferably ±10%, and most preferably ±5%.

The present invention provides a *Ganoderma lucidum* polysaccharide that can be used to improve insulin sensitivity. Through experimentations, the *G. lucidum* polysaccharide of the present invention is shown to be able to effectively reduce fasting serum insulin, fasting blood glucose, insulin resistance and glucose intolerance in a subject. Generally, the polysaccharide described herein can be administered daily for two months to mammals and humans at a dose of 0.001 mg/kg to 1 g/kg of body weight and can effectively reduce insulin resistance of the treated mammals and humans. Preferably, 0.0019 g of the polysaccharide is given daily for two months to a mouse (with an average weight of 30 g) while 4.53 g (0.0646 g/kg) of the polysaccharide is given to a human (with an average weight of 70 kg). Details of the invention are provided below.

First, the method used to isolate the *G. lucidum* polysaccharide sub-fraction possessing insulin-sensitizing effects is described. Then, the polysaccharide sub-fraction of the present invention is characterized, followed by a presentation of the experimentations showing the insulin-sensitizing effects of the isolated *G. lucidum* polysaccharide sub-fraction on fasting serum insulin, fasting blood glucose, insulin resistance (HOMA-IR), and the oral glucose tolerance test in mice.

Example 1

Preparation of the Polysaccharide Extracts and Sub-Fractions Isolated from *Ganoderma lucidum*

According to the present invention, *Ganoderma lucidum* polysaccharide having a molecular weight above 135 kDa can effectively reduce hyperglycemia and promote insulin sensitivity in a subject. The *G. lucidum* polysaccharide of the present invention can be added to the diet of the subject as a drink, a daily supplement, or a food, without having to modify the existing lifestyle, or without incurring in toxicity or other unfavorable health conditions.

1.1 Preparation of *G. lucidum* Water Extracts

Figure 1:
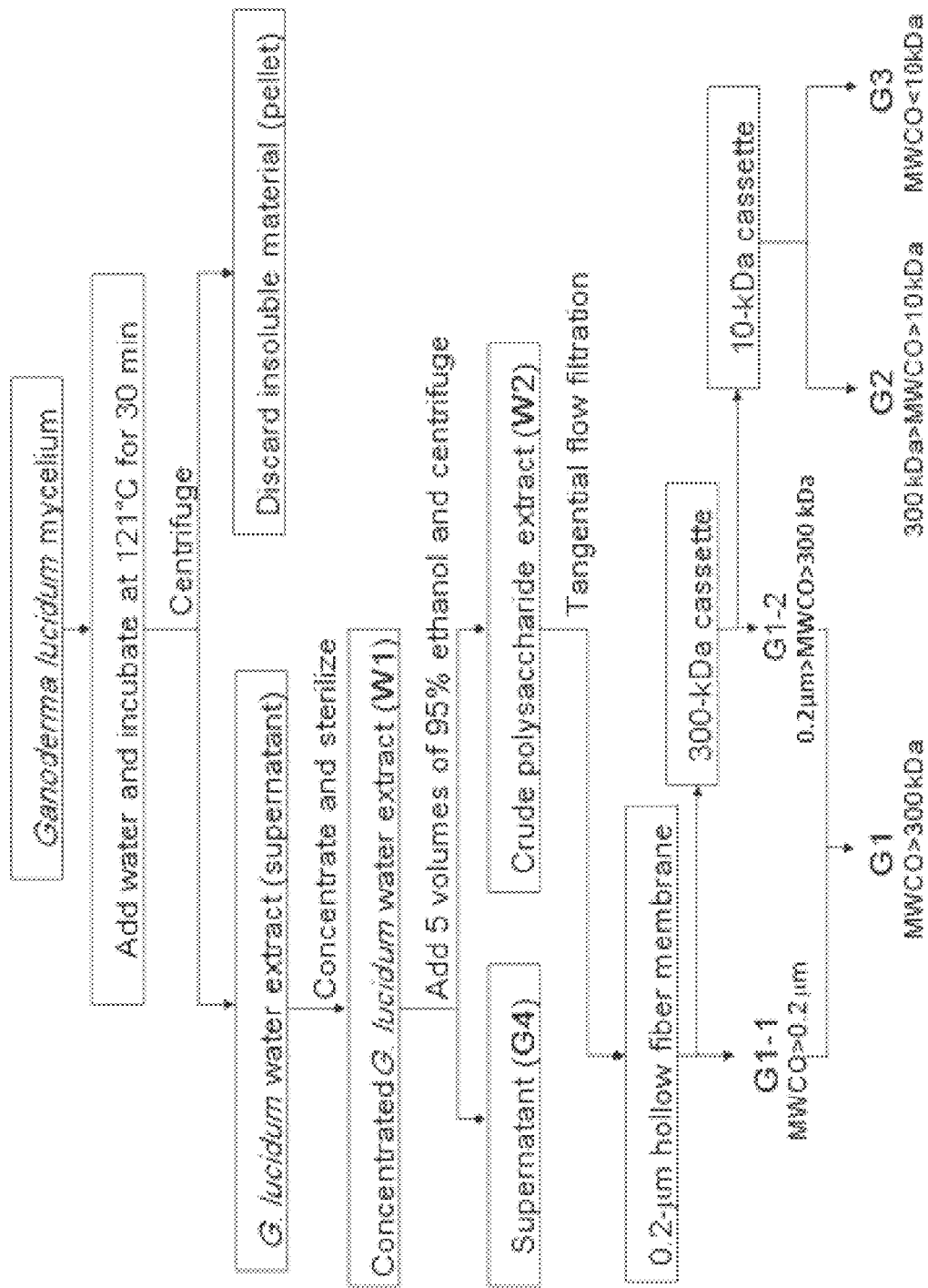
FIG. 1 shows a simplified flowchart for the isolation of *Ganoderma lucidum* water extracts and polysaccharide sub-fractions described in the present invention.

FIG. 1 illustrates the method used to isolate the polysaccharide from *G. lucidum* mycelium. Firstly, a water extract is prepared by mixing 500 g of dried *G. lucidum* mycelium obtained from Chang Gung Biotechnology (Taipei, Taiwan) with 10 liters of distilled water using a 20 liter-stirred tank reactor. The 5% (w/v) mixture is agitated at a speed of 150 revolutions per minute for 30 min at 121° C. The mixture is then centrifuged to remove insoluble material and obtain a *G. lucidum* water extract. The supernatant is concentrated to a final volume of 2.5 liters using a vacuum concentrator. The concentrated supernatant is sterilized at high temperature and high pressure in an autoclave for 20 min to obtain a 20% (w/v) concentrated *G. lucidum* water extract (labeled as W1, see FIG. 1).

1.2 Preparation of *G. lucidum* Crude Polysaccharide Extract

As shown in FIG. 1, 120 mL of the W1 20% (w/v) concentrated *G. lucidum* water extract (which contains 6.03 g of total water-soluble carbohydrates; see Table 1) is mixed with 5 volumes (600 mL) of 95% ethanol, and incubated at 4° C. for 16 hours to induce the precipitation of crude polysaccharide. The mixture is centrifuged to obtain a supernatant and a precipitate (pellet). The supernatant is removed, while 120 mL of 70% ice-cold ethanol is used to wash and resuspend the precipitate to obtain a mixture, and the mixture is centrifuged to obtain a supernatant and a precipitate (pellet). The supernatants from three such washing-resuspension-centrifugation steps are combined to give a supernatant of 1,050 mL (labeled as G4, with total water-soluble carbohydrates of 2.82 g; see Table 1). The crude polysaccharide precipitate (pellet) is dissolved into 1,000 mL of distilled water and concentrated to a final volume of 700 mL using the vacuum concentrator in order to remove residual ethanol. Finally, distilled water is added to obtain a fraction with a final volume of 2,400 mL (labeled as W2, with total water-soluble polysaccharides of 3.21 g; see Tables 1 and 2).

1.3 Fractionation of *G. lucidum* Crude Polysaccharide Extract 2,400 mL of *G. lucidum* crude polysaccharide extract is placed into a beaker and incubated at 50° C. in a water bath. The extract is fractionated by using a tangential flow filtration (TFF) system (KrosFlo, Spectrum Laboratories) with a 0.2-μm hollow fiber membrane (1,500 cm², PES). The trans-membrane pressure (TMP) is set at 15-16 psi. 600 mL of distilled water is added into the retentate during filtration. Addition of water is repeated two times (a total of 1,800 mL distilled water is added to the retentate). A 650 mL retentate (labeled as G1-1, with total water-soluble polysaccharides of 1.26 g) and 3,600 mL of filtrate are obtained this way.

The above-mentioned 3,600 mL of 0.2-nm hollow fiber membrane filtrate obtained is placed into a beaker and incubated at 50° C. in a water bath. The 3,600 mL of filtrate is fractionated by using TFF with a 300-kDa cassette membrane (50 cm², PES). The TMP is set between 16-18 psi. 600 mL of distilled water is added into the retentate during filtration when the retentate ranges from 1,000 mL to 1,200 mL. A 950 mL retentate (labeled as G1-2, with total water-soluble polysaccharides of 0.60 g) and 3,600 mL filtrate are obtained. Fractions G1-1 and G1-2 are combined to obtain a final fraction of 1,600 mL (labeled as G1, with total water-soluble polysaccharides of 1.86 g; see Table 2).

The above-mentioned 3,600 mL of the 300-kDa filtrate is placed into a beaker and incubated at 50° C. in a water bath. The 300-kDa filtrate is fractionated using TFF with a 10-kDa cassette membrane (50 cm², PES). The TMP is set between 16-18 psi. 600 mL of distilled water is added into the retentate during filtration when the retentate ranges from 1,000 mL to 1,200 mL. The operation is repeated to obtain 970 mL of 10 kDa-to-300 kDa retentate (labeled as G2, with total water-soluble polysaccharides of 1.01 g; see Table 2) and 3,600 mL of 10 kDa filtrate (labeled as G3, with total water-soluble polysaccharides of 0.34 g; see Table 2).

The G1, G2, G3 and G4 sub-fractions are concentrated separately using the vacuum concentrator to obtain a final volume of 110 mL. Concentrated sub-fractions are sterilized at 121° C. in an autoclave for 20 min 1.4 Total Water-Soluble Carbohydrates and Polysaccharides Content of the Isolated G. lucidum Extracts and Sub-Fractions The phenol-sulfuric acid assay is used to determine the level of total water-soluble carbohydrates and polysaccharides found in the isolated G. lucidum extracts and polysaccharide sub-fractions, which include the 20% (w/v) concentrated G. lucidum water extract (labeled as W1, 120 mL), the G. lucidum crude polysaccharide extract (labeled as W2, 2400 mL), a combination of the retentate of the 0.2-nm hollow fiber filtration and the 300-kDa-cutoff pore membrane filtration (labeled as G1; 1,600 mL), the retentate of the 10 kDa cassette membrane (labeled as G2; 970 mL), the filtrate of the 10-kDa-cutoff pore membranes (labeled as G3; 3,600 mL), and the supernatants from the 95% ethanol precipitation and wash process (labeled as G4; 1,050 mL). To establish the standard curve for the phenol-sulfuric acid assay, glucose standard solutions are prepared at concentrations of 0, 0.02, 0.04, 0.06, 0.08, 0.10, 0.12, 0.14, 0.16, 0.18, and 0.20 mg/mL. 200 μl of each solution is placed into 1.5-mL tubes. 200 μl of 5% phenol is added and the solution is mixed. 1 mL of sulfuric acid is added and the solution is mixed. After incubation for 20 min, the absorbance at 490 nm is monitored using a spectrophotometer and the calibration curve of glucose standard solution is prepared. The calculated R squared is higher than 0.99. The sample solutions are appropriately diluted and 200 μl of each diluted solution is placed into 1.5-mL tubes. Phenol and sulfuric acid are added as above and the absorbance is monitored. The value obtained is plotted onto the calibration curve to determine the concentration of total water-soluble carbohydrates or total water-soluble polysaccharides of the samples.

Total water-soluble carbohydrates and polysaccharides found in the G. lucidum polysaccharide extracts and sub-fractions are shown in Table 1 and 2. Table 1 and 2 show that the W2 crude polysaccharide extract isolated from G. lucidum contains 3.21 g of water-soluble polysaccharides and that the G1 sub-fraction contains 1.86 g of polysaccharides with a molecular weight above 300 kDa, which accounts for 57.9% of the total G. lucidum crude polysaccharide extract (W2).

TABLE 1

Total water-soluble carbohydrates and polysaccharides of the isolated G. lucidum extracts and sub-fractions

| Fraction | | Content (g) | Percentage (%) |
|---|---|---|---|
| W1 | Total water-soluble carbohydrates | 6.03 | 100 |
| W2 | Total water-soluble polysaccharides | 3.21 | 53.2 |
| G4 | Mono-, di-, oligo-saccharides | 2.82 | 46.8 |

TABLE 2

Polysaccharide distribution of the G. lucidum crude polysaccharide extract (W2) and sub-fractions

| Fraction | | Content (g) | Percentage (%) |
|---|---|---|---|
| W2 | Total water-soluble crude polysaccharides | 3.21 | 100 |
| G1 | MWCO > 300 kDa | 1.86 | 57.9 |
| G2 | 300 kDa > MWCO > 10 kDa | 1.01 | 31.5 |
| G3 | 10 kDa > MWCO | 0.34 | 10.6 |

MWCO: molecular weight cut-off 1.5 Monosaccharide Analysis of G. lucidum G1 Polysaccharide Sub-Fraction High pH anion exchange chromatography-pulsed amperometric detection (HPAEC-PAD) is used to analyze the monosaccharide components of each fraction. Monosaccharide standard solutions of L-fucose, L-rhamnose, D-galactosamine, D-glucosamine, D-arabinose, D-galactose, D-glucose and D-mannose are prepared at 0.1, 0.5, 1, 2 and 5 mg/L. 25 μL of each solution is used for ionic chromatography analysis with the HPAEC-PAD Dionex ICS-5000 System (CarboPacPA1 column with an internal diameter of 4×250 mm, Thermo Scientific). Elution is performed with 16 mM NaOH (which represents a mixture of water and 200 mM NaOH at the volume ratio of 92:8) and the flow rate is set at 1 mL/min. The temperature of column oven is set at 30° C. After 30 min of analysis, the peak area of each monosaccharide standard is determined at 0.1, 0.5, 1, 2 and 5 mg/L. The standard curve of the seven monosaccharide standards is established (calculated $R^2 > 0.99$).

Figure 2:
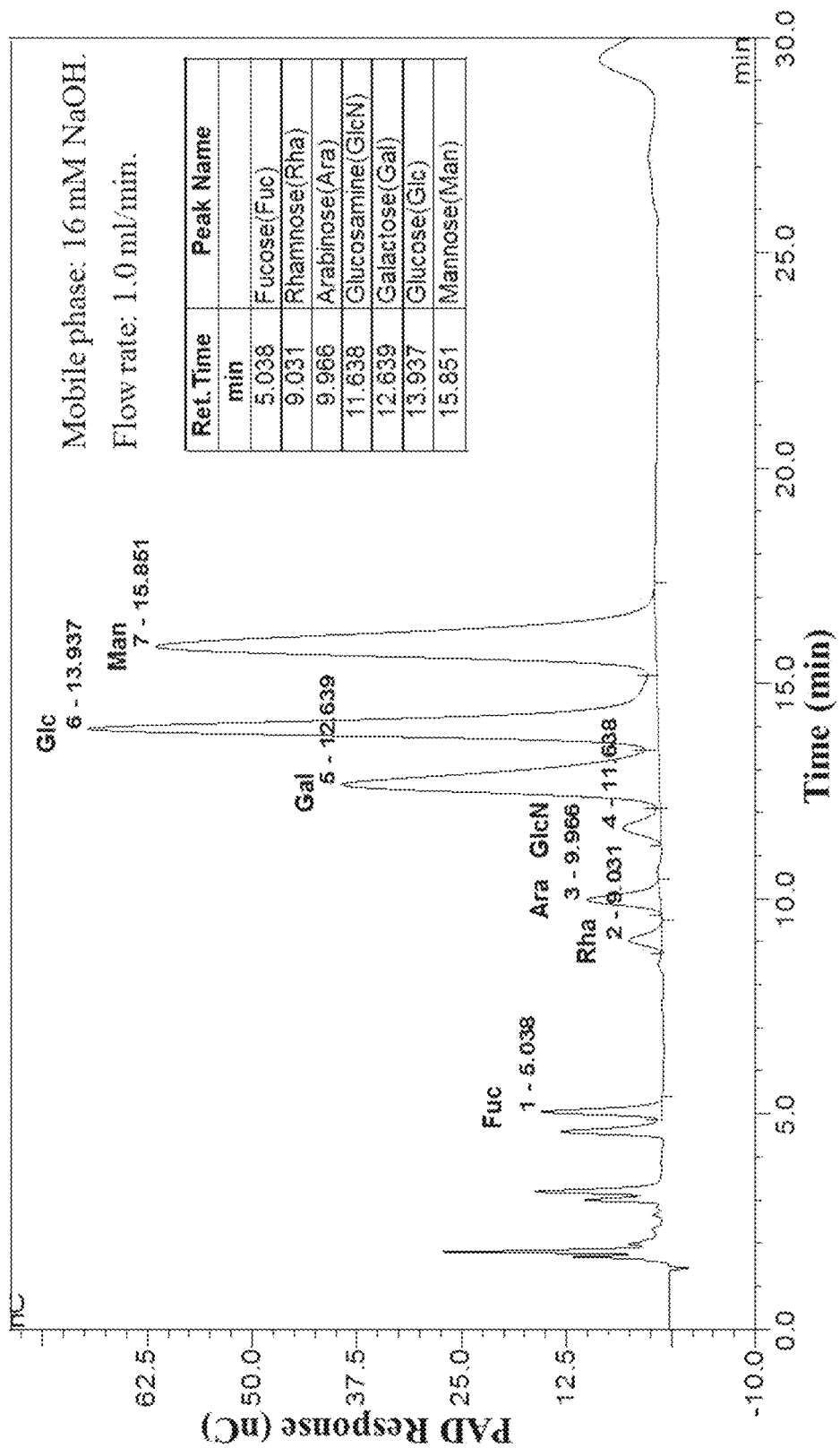
FIG. 2 shows the monosaccharide analysis of *G. lucidum* polysaccharide sub-fraction G1. The analysis was performed using high-performance anion exchange chromatography with pulsed amperometric detection (HPAEC-PAD).

0.21 mL of the G1 sub-fraction (3 mg of total water-soluble polysaccharides) is added to 2.79 mL of distilled water and hydrolyzed with 1.33 mL of trifluoroacetic acid at 112° C. for 12 hours. The acid is removed by co-distillation with water after hydrolysis is completed. Each hydrolysate (1 mg) is dissolved in pure water (1 mg/mL). After a 4-fold dilution of the hydrolysate with pure water (0.25 mg/mL), 25 μL of the hydrolysate solution is used for ionic chromatography analysis by HPAEC-PAD system as described above. Elution is performed with 16 mM NaOH as above. After 30 min of analysis, the analytic HPAEC-PAD profile of the hydrolysate solution is acquired. The monosaccharide components and molar ratio of the G1 sub-fraction is determined by comparison with the standard curve. The G1 sub-fraction is found to consist of 2.8% fucose, 2.5% rhamnose, 2.9% arabinose, 1.1% glucosamine, 16.9% galactose, 26.3% glucose, and 47.5% mannose (FIG. 2, Tables 3 and 4).

TABLE 3

Monosaccharide analysis of the *G. lucidum* G1 polysaccharide sub-fraction using HPAEC-PAD

| Monosaccharide | Percentage (%) |
|---|---|
| Fucose | 2.8 |
| Rhamnose | 2.5 |
| Arabinose | 2.9 |
| Glucosamine | 1.1 |
| Galactose | 16.9 |
| Glucose | 26.3 |
| Mannose | 47.5 |

TABLE 4

Monosaccharide molar ratio of the G1 polysaccharide sub-fraction isolated from *G. lucidum*

| Monosaccharide | Molar ratio |
|---|---|
| Fucose | 0.07 |
| Rhamnose | 0.06 |
| Arabinose | 0.07 |
| Glucosamine | 0.02 |
| Galactose | 0.36 |
| Glucose | 0.55 |
| Mannose | 1 |

1.6 Molecular Weight Distribution of the G1 Polysaccharide Sub-Fraction Isolated from *G. lucidum*

The molecular weight of the isolated G1 polysaccharide sub-fraction is analyzed using size-exclusion chromatography (SEC) and high performance liquid chromatography with refractive index (RI), differential viscosity (DV) and light scattering (LS) detectors (Waters RI detector model 2410 and dual detector Viscotek 270). Dextran 670 (667,800 Da) at 1.5 mg/mL is used as a standard marker to calibrate the system. 100 µL of sample is analyzed on two connected GPC columns (TSKgel G5000PW×L and TSKgel G6000PW×L; 7.8×300 mm) Elution is performed with 0.02% $NaNO_3$ and the flow rate is set at 0.8 mL/min (column temperature of 22° C.).

Molecular weight parameters of the G1 sub-fraction (containing 7.5 mg/mL of total water-soluble polysaccharides) are calculated using the OmniSEC software (Viscotek) and the following equations:

Mn: number average molecular weight $$Mn = \frac{\Sigma NiMi}{\Sigma Ni}$$

Mw: weight average molecular weight $$Mw = \frac{\Sigma NiMi^2}{\Sigma NiMi}$$

Mz: higher average molecular weight $$Mz = \frac{\Sigma NiMi^3}{\Sigma NiMi^2}$$

Figure 3:
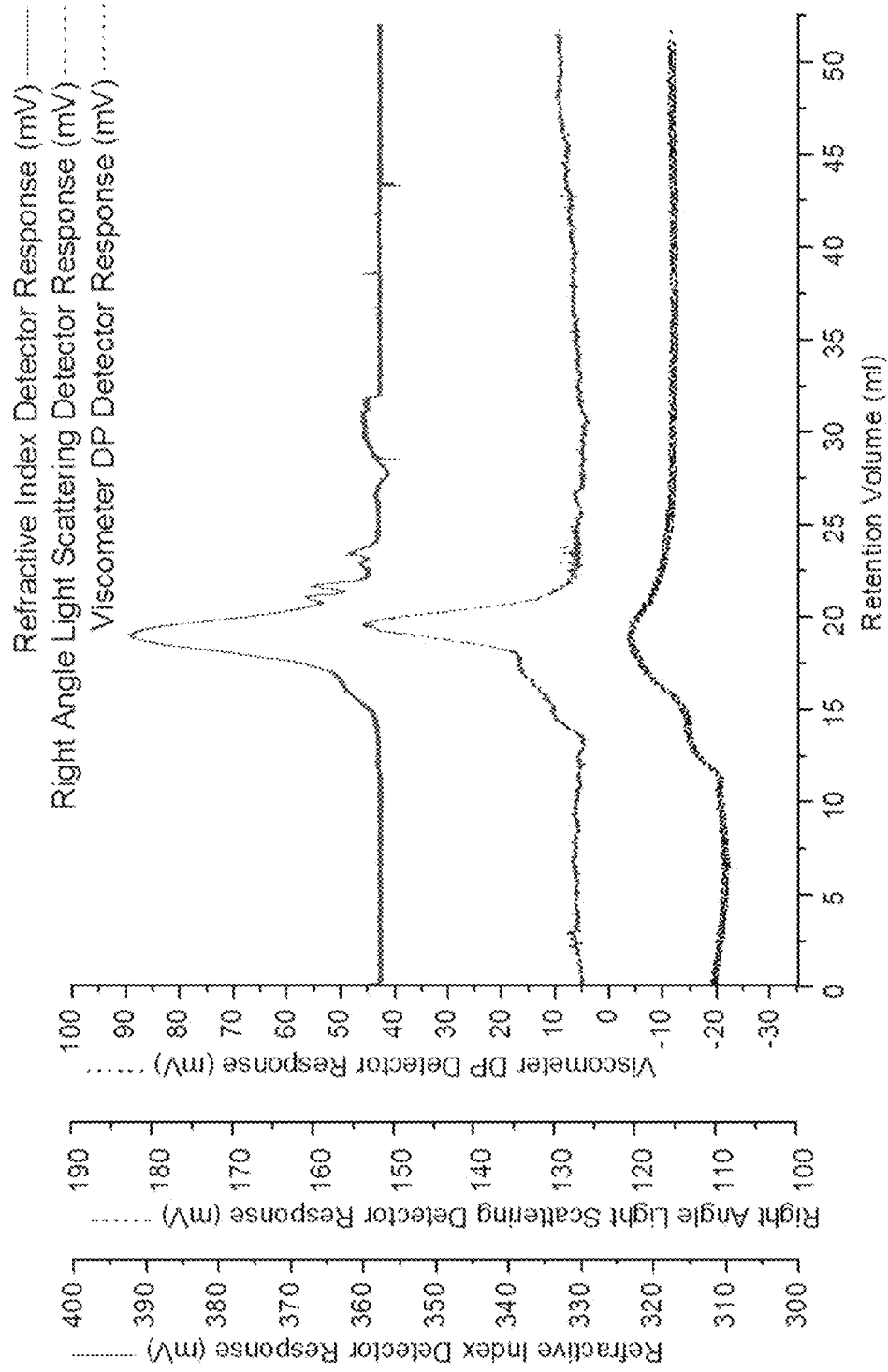
FIG. 3 shows the gel permeation chromatogram of *G. lucidum* polysaccharide sub-fraction G1 described in the present invention.
Figure 4:
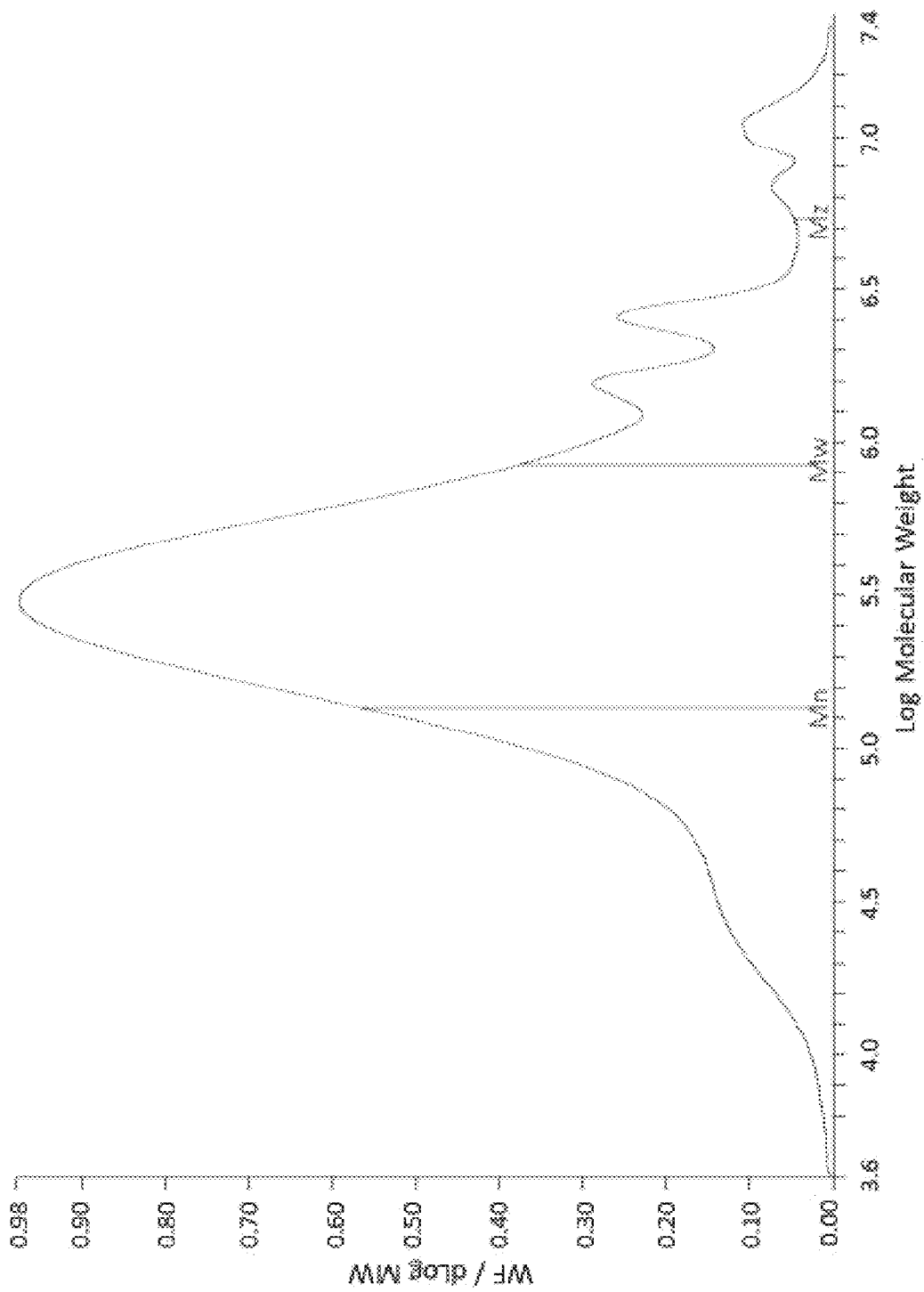
FIG. 4 shows the graph of weight fraction (WF)/d Log molecular weight (MW) versus log MW of *G. lucidum* polysaccharide sub-fraction G1.
Figure 5:
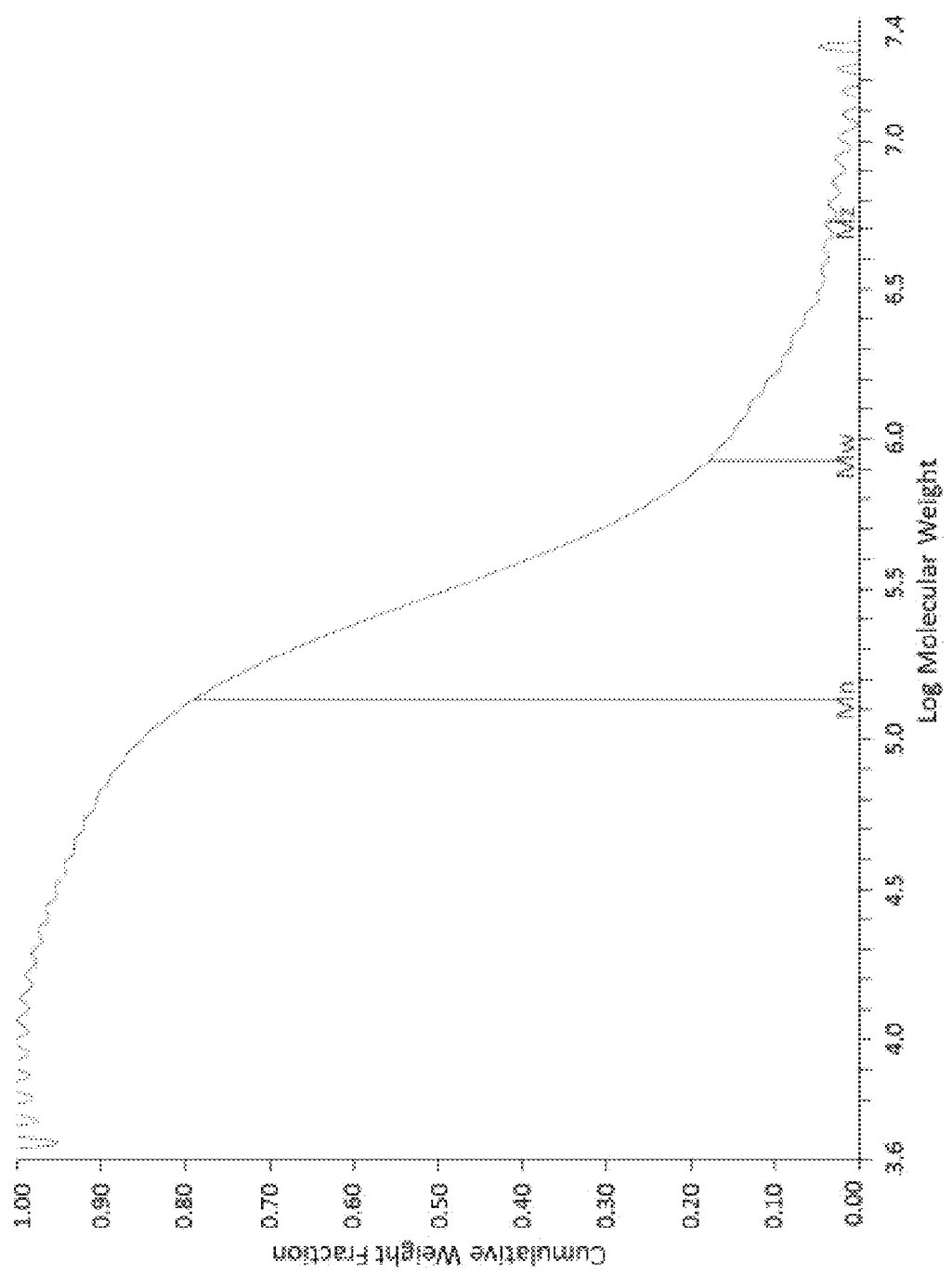
FIG. 5 shows the graph of cumulative weight fraction versus log MW of *G. lucidum* polysaccharide sub-fraction G1.

Mp: molecular weight at peak maximum, which is measured at the point of the molecular weight distribution maximum
Mi: molecular weight of a chain
Ni: number of chains of that molecular weight Based on RI-DV-LS analysis of the G1 sub-fraction (FIG. 3), the molecular weight distribution of this sub-fraction is determined (FIG. 4). Based on these experimental data, the following parameters are calculated: Mn (number average molecular weight), 135,395 Da; Mw (weight average molecular weight), 846,622 Da; Mz (higher average molecular weight), 5,364,000 Da; and Mp (molecular weight at peak maximum), 309,436 Da. The cumulative molecular weight fraction is shown in FIG. 5. Based on these data (FIG. 5), the cumulative weight fraction values of Mn and Mw are 0.79 and 0.18, corresponding to molecular weights ranging between 135,395 Da (Mn) and 846,622 Da (Mw), and the polydispersity index (Mw/Mn) is 6.25; the G1 sub-fraction represents approximately 61% of the total polysaccharide weight.

Even though the G1 polysaccharide sub-fraction isolated from *G. lucidum* represents a retentate obtained with a 300-kDa cut-off membrane, biopolymers such as polysaccharides are known to aggregate under these conditions, an observation which may explain why the calculated molecular weight of the polysaccharide found in the G1 sub-fraction is lower than the molecular weight cut-off of the membranes used to isolate this sub-fraction. Based on the information derived from FIG. 4, the polysaccharide of the G1 sub-fraction described in the present invention has a molecular weight above 135 kDa.

Example 2

Effects of the Isolated *G. lucidum* Polysaccharide Sub-Fractions on Insulin Function in High-Fat Diet-Fed Mice The effects of *Ganoderma lucidum* polysaccharide sub-fractions are tested on mice fed a high-fat diet (HFD), which is commonly used as a model to study insulin resistance and type 2 diabetes. C57BL/6NCrlBltw mice are fed with either standard chow (13.5% of energy from fat) or HFD (60% of energy from fat) and treated daily with 100 µL of polysaccharide sub-fraction (G1, G2, G3, or G4) or distilled water by intragastric gavage for two months (n=5 mice for each group). The mouse groups comprise the following: HFD+G1, HFD+G2, HFD+G3, HFD+G4, HFD, Chow+G1, Chow+G2, Chow+G3, Chow+G4, and Chow. FIGS. 6A to 6D show the effects produced by the *G. lucidum* polysaccharide sub-fractions on fasting serum insulin, fasting blood glucose, HOMA-IR assessment (a measure of insulin resistance), and the oral glucose tolerance challenge.

Figure 6A:
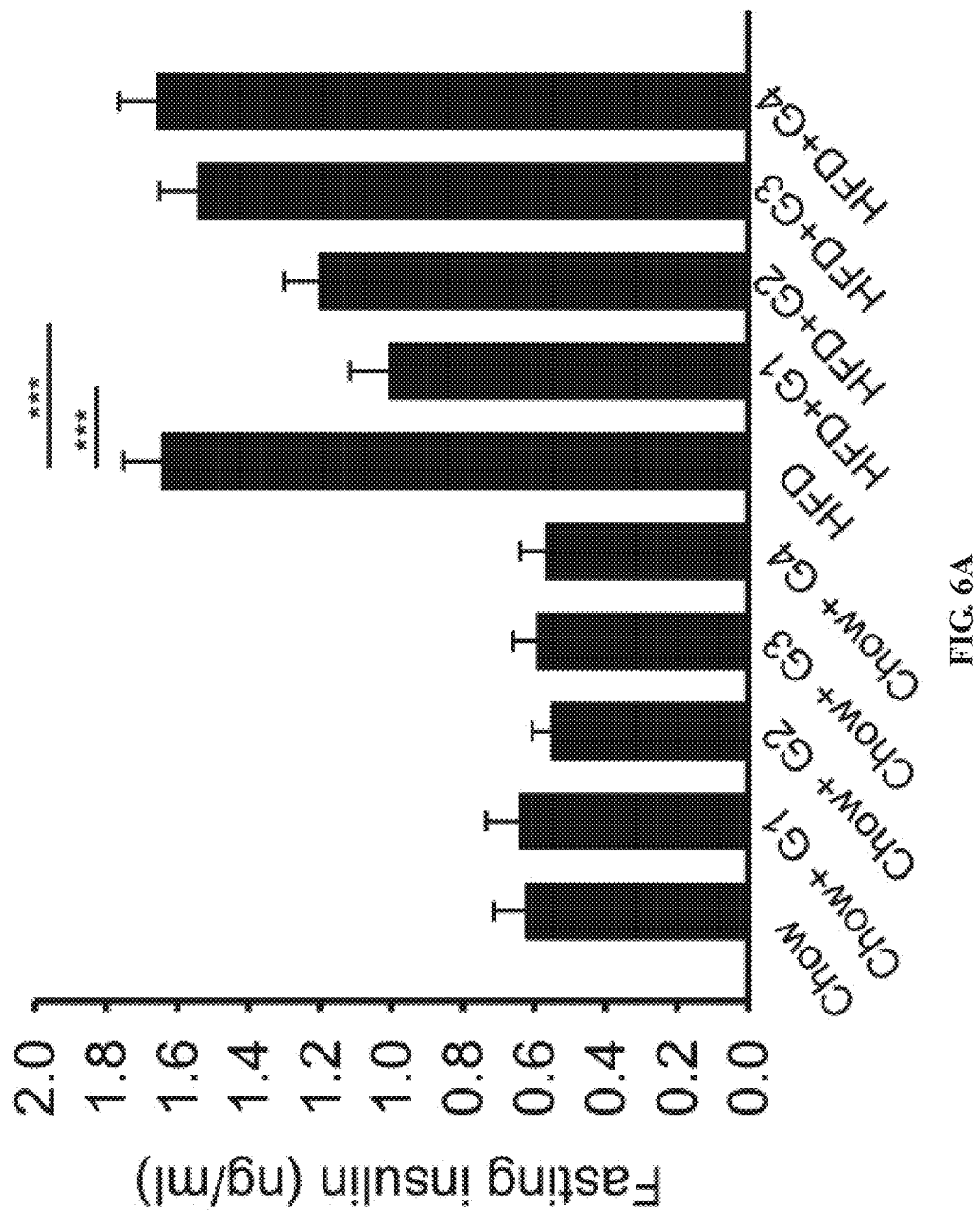
FIG. 6A shows the effects of the polysaccharide sub-fractions isolated from *G. lucidum* on fasting serum insulin, wherein fasting serum insulin concentrations were determined in 5 µL of serum using a commercial ELISA kit based on the manufacturer's instructions. Statistical significance was analyzed using Student's t test (***P<0.001).
Figure 6B:
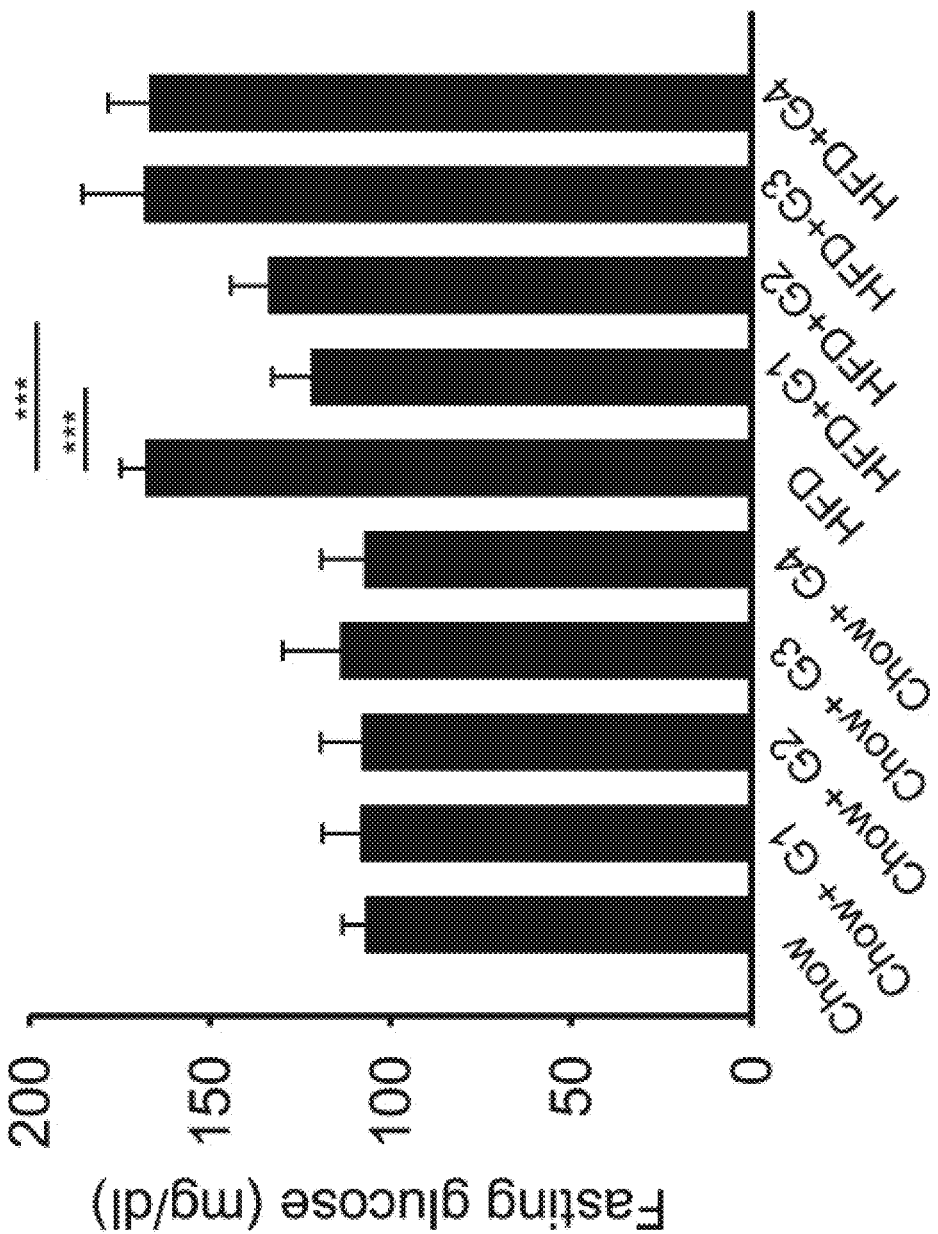
FIG. 6B shows the effects of the polysaccharide sub-fractions isolated from *G. lucidum* on fasting blood glucose, wherein fasting blood glucose was determined using a standard glucose meter and blood collected from the tip of the tail vein. Statistical significance was analyzed using Student's t test (***P<0.001).
Figure 6C:
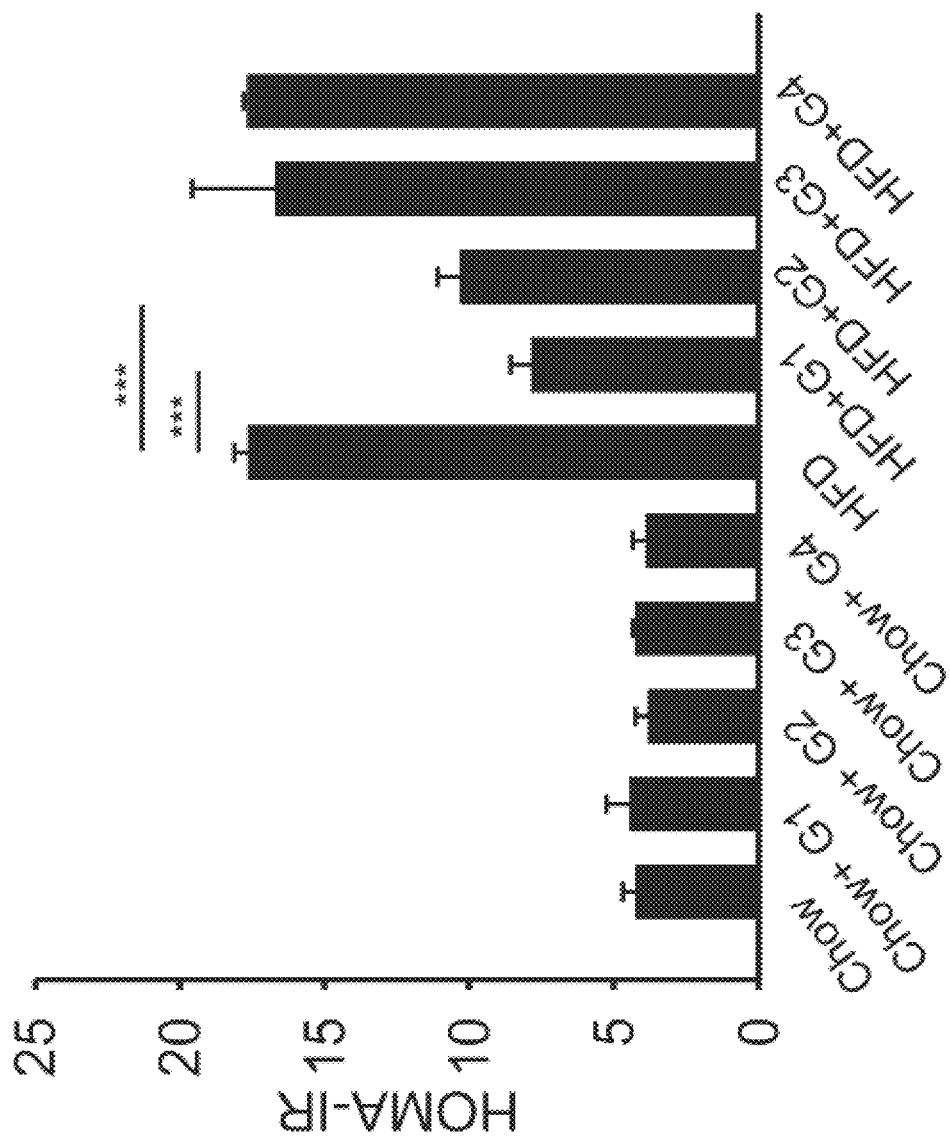
FIG. 6C shows the effects of the polysaccharide sub-fractions isolated from *G. lucidum* on homeostatic model assessment of insulin resistance (HOMA-IR). HOMA-IR, which represents a measure of insulin resistance and pancreatic beta-cell functions, was calculated using a standard protocol. Statistical significance was analyzed using Student's t test (***P<0.001).
Figure 6D:
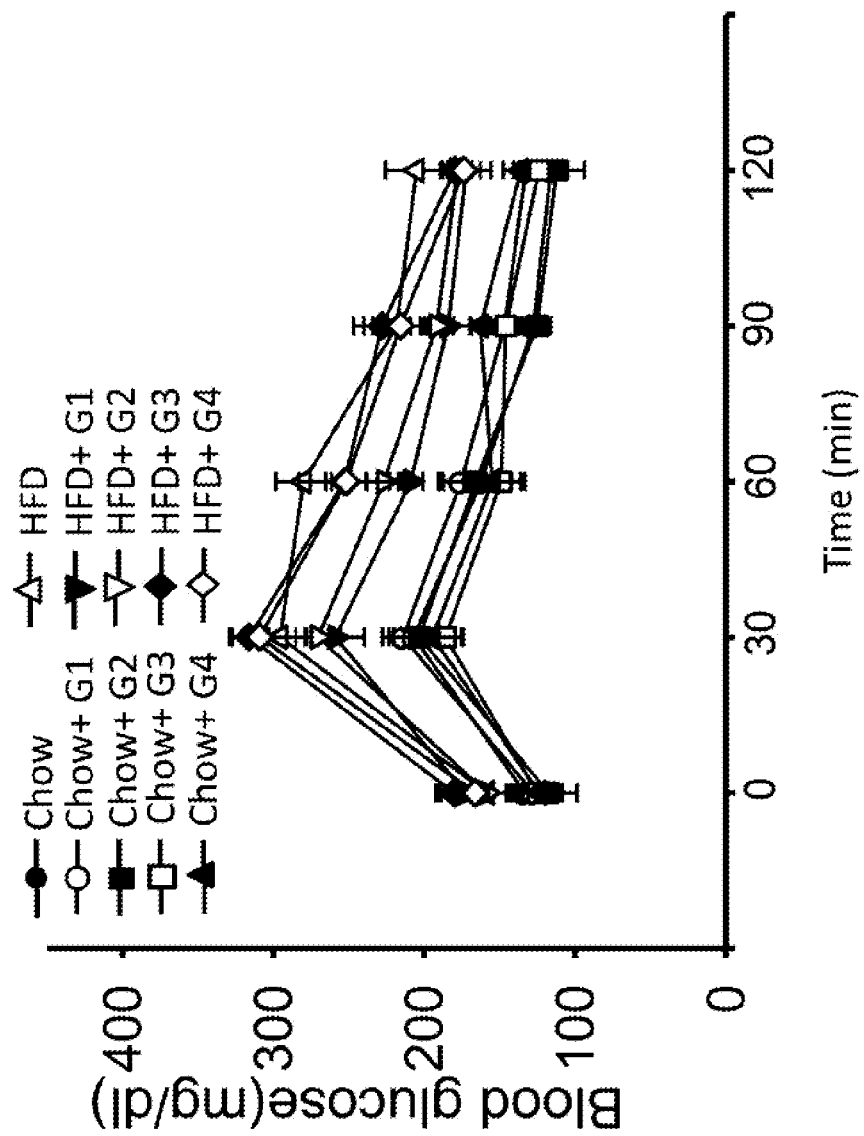
FIG. 6D shows the effects of the polysaccharide sub-fractions isolated from *G. lucidum* on oral glucose tolerance test. Blood glucose levels were monitored following an oral glucose challenge (3 g/kg) administered at time 0.
Figure 6E:
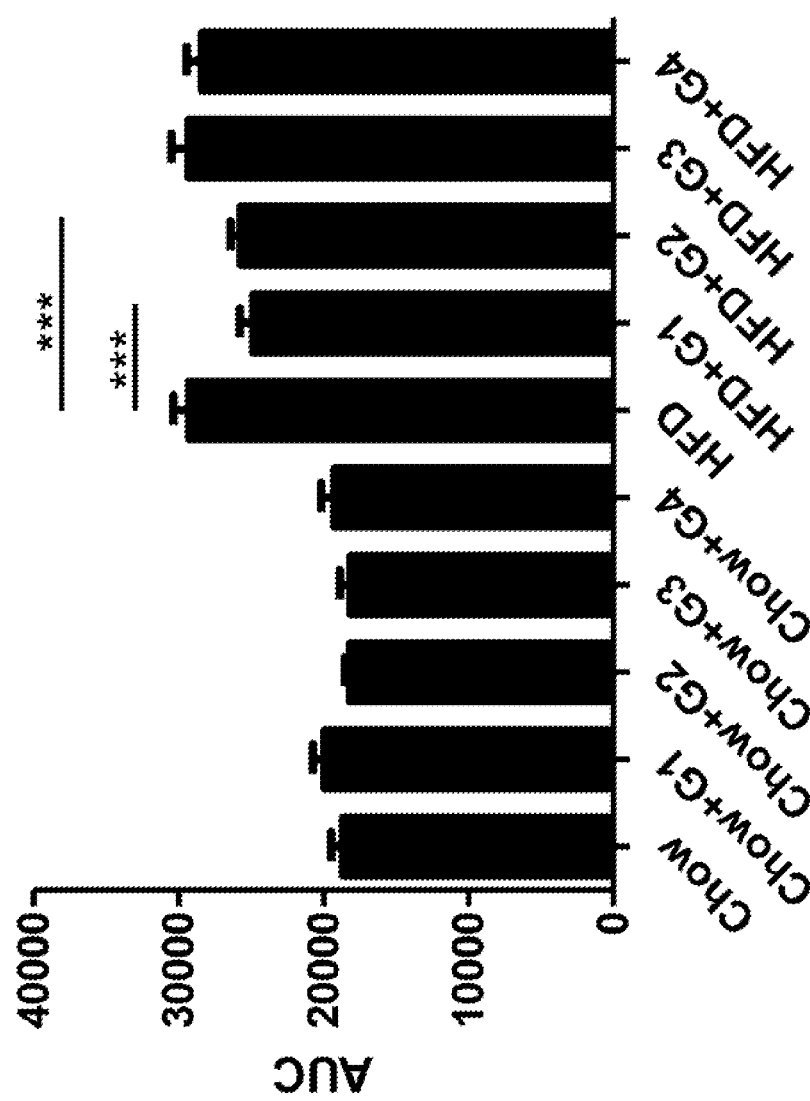
FIG. 6E shows area under the curve (AUC) determined for the oral glucose tolerance test performed in FIG. 6D. Statistical significance was analyzed using Student's t test (***P<0.001).

As shown in FIGS. 6A and 6B, feeding with a HFD increases fasting insulin and glucose levels compared to chow feeding. On the other hand, supplementation with the G1 or G2 sub-fractions considerably reduces fasting insulin and glucose levels in HFD-fed mice. Insulin resistance was also assessed using HOMA-IR monitoring. As shown in FIG. 6C, HFD feeding increases insulin resistance compared to the chow-fed group. However, the G1 and G2 sub-fractions reduce insulin resistance in a statistically significant manner compared to the HFD group (FIG. 6C). HFD-fed mice also show a pronounced increase of blood glucose levels in the oral glucose tolerance test, while HFD-fed mice supplemented with the G1 and G2 polysaccharide sub-fractions show reduced blood glucose levels compared to HFD feeding (FIG. 6D, the top panel shows blood glucose levels while the lower panel shows the area under the curves shown in the top panel). Notably, the G1 sub-fraction produces better insulin-sensitizing effects than the G2 sub-fraction (FIGS. 6A-D), which is the reason why the G1 sub-fraction is chosen in the present invention as the most effective preparation producing insulin-sensitizing effects in animals.

G. lucidum polysaccharide sub-fraction G1 can therefore reduce fasting serum insulin content (FIG. 6A), fasting blood glucose (FIG. 6B), insulin resistance (FIG. 6C), and glucose intolerance (FIG. 6D) in HFD-fed mice. Given that the polysaccharide content of sub-fraction G1 is 1.94 g/100 mL, the effective daily amount or dosage of G. lucidum polysaccharide required to produce insulin-sensitizing effects in mice (with an average weight of 30 g) is 0.0019 g/mouse (for a period of two months). Accordingly, the effective daily amount or dosage of G. lucidum polysaccharide sub-fraction G1 that would produce similar effects in a human subject (with an average weight of 70 kg) is estimated at 4.53 g/individual, which is equal to 0.0646 g/kg.

The present invention provides a method to isolate a polysaccharide sub-fraction from G. lucidum, and this sub-fraction can reduce insulin and glucose levels in the blood of mammals, under either the fasting state or following a glucose challenge. Therefore, the G. lucidum polysaccharide sub-fraction described in the present invention has obvious commercial value and applications for the development of novel strategies to prevent or treat type 2 diabetes mellitus, insulin resistance, and related conditions such metabolic syndrome. Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for improving insulin sensitivity, comprising administrating an effective amount of a polysaccharide isolated from *Ganoderma lucidum* mycelium to a subject in need thereof, wherein the polysaccharide has a molecular weight above 135 kDa and consists of mannose, glucose, galactose, fucose, rhamnose, arabinose, and glucosamine.

2. The method of claim 1, wherein a weight ratio of fucose, rhamnose, arabinose, glucosamine, galactose, glucose, and mannose in the polysaccharide ranges between 2:2:2:1:16:26:47 and 3:3:3:1:17:27:48.

3. The method of claim 1, wherein the molecular weight of the polysaccharide ranges from 135 kDa to 5,364 kDa, with a polydispersity index (Mw/Mn) of 6.25.

4. The method of claim 1, wherein the average molecular weight of the polysaccharide is 846 kDa.

5. The method of claim 1, wherein the polysaccharide reduces fasting blood insulin and fasting blood glucose in a subject.

6. The method of claim 1, wherein the polysaccharide reduces insulin resistance in a subject.

7. The method of claim 1, wherein the effective amount of the polysaccharide given is from 0.001 mg/kg to 1 g/kg per day.

8. The method of claim 1, wherein the effective amount of the polysaccharide is 0.0646 g per kilogram of body weight.

* * * * *